(12) United States Patent  (10) Patent No.: US 6,746,458 B1
Cloud  (45) Date of Patent: Jun. 8, 2004

(54) MESH MATERIAL TO REPAIR HERNIAS

(76) Inventor: William G. Cloud, 6600 Ciscayne Pl., Charlotte, NC (US) 28211

(*) Notice: Subject to any disclaimer, the term of this patent is extended or adjusted under 35 U.S.C. 154(b) by 244 days.

(21) Appl. No.: 09/657,675
(22) Filed: Sep. 7, 2000
(51) Int. Cl.$^7$ .............................................. A61B 17/08
(52) U.S. Cl. ..................... 606/151; 606/153; 602/41
(58) Field of Search ................. 606/151, 213, 606/216; 128/95.1, 96.1

(56) References Cited

U.S. PATENT DOCUMENTS

| | | | |
|---|---|---|---|
| 3,553,737 A | 1/1971 | Bauman | 3/1 |
| 3,842,439 A | 10/1974 | Connelly et al. | 3/1 |
| 3,914,801 A | 10/1975 | Dick et al. | 3/1 |
| 4,092,739 A | 6/1978 | Clemens et al. | 3/1 |
| 4,193,137 A | 3/1980 | Heck | 3/1.4 |
| 4,279,248 A | 7/1981 | Gabbay | 128/92 |
| 4,347,847 A | 9/1982 | Usher | 128/334 |
| 4,452,245 A | 6/1984 | Usher | 128/334 |
| 4,520,821 A | 6/1985 | Schmidt et al. | 128/334 |
| 4,633,873 A | 1/1987 | Dumican et al. | 128/334 |
| 4,652,264 A | 3/1987 | Dumican | 623/1 |
| 4,655,221 A | 4/1987 | Devereux | 128/334 |
| 4,838,884 A | 6/1989 | Dumican et al. | 604/364 |
| 5,002,551 A | 3/1991 | Linsky et al. | 606/151 |
| 5,021,059 A * | 6/1991 | Kensey et al. | 606/213 |
| 5,141,515 A * | 8/1992 | Eberbach | 606/151 |
| 5,220,928 A | 6/1993 | Oddsen et al. | 128/898 |
| 5,290,217 A | 3/1994 | Campos | 600/37 |
| 5,290,297 A | 3/1994 | Phillips | 606/144 |
| 5,333,624 A | 8/1994 | Tovey | 128/897 |
| 5,379,754 A | 1/1995 | Tovey et al. | 128/4 |
| 5,496,345 A * | 3/1996 | Kieturakis et al. | 606/192 |
| 5,503,638 A | 4/1996 | Cooper et al. | 623/11 |
| 5,634,931 A | 6/1997 | Kugel | 606/151 |
| 5,725,577 A | 3/1998 | Saxon | 623/11 |
| 5,743,917 A | 4/1998 | Saxon | 623/11 |
| 5,766,246 A | 6/1998 | Mulhauser et al. | 606/151 |
| 5,824,082 A * | 10/1998 | Brown | 623/11.11 |
| 5,855,591 A | 1/1999 | Bierman | 606/232 |
| 5,868,762 A | 2/1999 | Cragg et al. | 606/144 |
| 5,911,726 A | 6/1999 | Belknap | 606/144 |
| 5,916,225 A | 6/1999 | Kugel | 606/151 |
| 5,922,026 A | 7/1999 | Chin | 623/11 |
| 6,042,592 A | 3/2000 | Schmitt | 606/151 |
| 6,090,116 A | 7/2000 | D'Aversa et al. | 606/151 |
| 6,425,924 B1 * | 7/2002 | Rousseau | 623/23.64 |
| 6,482,214 B1 * | 11/2002 | Sidor et al. | 606/151 |

* cited by examiner

Primary Examiner—Michael J. Milano
Assistant Examiner—D. Jacob Davis
(74) Attorney, Agent, or Firm—Womble Carlyle Sandridge & Rice, PLLC

(57) ABSTRACT

The present invention relates to surgically implantable devices that allow a surgeon to locate suture threads that are attached to the implantable device before it is implanted into a patient. The present invention addresses the need to grasp suture threads and pass them through body tissues by laparoscopic or endoscopic surgery, without the suture threads entangling or otherwise resisting the surgical procedure. The present invention encloses suture threads, each of which is attached by one end to an implantable device in suture housings. The present invention further includes novel pull-tabs that allow the grasping of a suture thread and extraction from a suture housing. The present invention also provides novel suture assemblies that may be attached to a surgically implantable device and methods of attaching, to a patient, surgically implantable device implants that have suture assemblies attached thereon.

32 Claims, 7 Drawing Sheets

MESH MATERIAL TO REPAIR HERNIAS

FIELD OF THE INVENTION

The present invention relates generally to surgical implants and suture assemblies for securing implants to patients. More specifically, the present invention relates to surgically implantable devices for the repair of hernias and surgical incisions, reconstructive surgery, prosthetic medical devices and suture assemblies attached thereto.

BACKGROUND

The structural integrity of a membrane or muscle may be compromised by a rupture or split resulting from physical strain combined with an inherent weakness of the tissue. Alternatively, a congenital abnormality may leave an opening in a membrane that would otherwise be closed during normal development. When damage or abnormalities of this nature occur to the abdominal wall, it provides an opportunity for an internal organ or other anatomical feature to protrude through the ruptured membrane as a hernia. The patient's symptoms can range from mild discomfort to acute pain, and the protruding organ itself can be compressed or constricted. The organ or that part thereof that protrudes through the body cavity wall can then undergo progressive deterioration. In the severest cases, the organ could become permanently damaged, with chronic health consequences for the patient. In the short term, a total or partial blockage of an organ such as an intestine can have an immediate impact on the general health of the patient.

A hernia, i.e. the protrusion of an organ through a tissue, may occur anywhere in the body. When in the lower abdominal area, it often involves penetration of the intestine into or through the abdominal wall. A frequently encountered hernia occurs in the region of the superficial inguinal ring of the groin region. When the intestine protrudes through the inguinal opening in the abdominal cavity wall, one has a direct or indirect inguinal hernia. A femoral hernia results from the intestine protruding through the abdominal wall in the region of the femoral ring.

Temporary relief from the symptoms of a hernia can be obtained by the patient wearing a truss device that applies external pressure against the abdomen in the region of the organ protrusion. This well-known and long-established treatment rarely, if ever, provides other than temporary relief from pain and more obvious discomfiture. Permanent relief typically requires invasive surgery to return the offending organ to its original and correct position, followed by the repair and reinforcement of the split or weakness in the abdominal wall.

The surgical procedure may be under local or general anathesia. Commonly, a large incision up to six inches long is made in the lower abdomen and the protruding organ, such as a region of the intestine, is retracted back out of the rupture and into the body cavity. The break in the body wall tissues can then be closed by suturing across the split or by pulling the sides of the split together, similar to the tying of a sack. The newly closed, but still weakened area of the body wall, may be reinforced by covering the repair with a flexible mesh material that is sutured or stapled into position. Still, the repaired hernia represents a mechanically weaker region of the internal abdominal wall. Accordingly, a "recurrent hernia" can subsequently occur due to the breakdown of the repaired injury. An additional possible complication of this procedure is the occurrence of an "incision hernia" where the surgical entry into the abdomen has reduced the integrity of the abdominal wall, and allowed another hernia to later develop at that site.

Conventional surgical procedures for hernia repair are traumatic for the patient. Not only does the surgical incision disrupt still further the mechanical integrity of the abdominal wall, but general surgical procedures may also lead to post-operative complications, including infection, hemorrhage, and damage to the underlying organs, musculature and nerves, that are associated with all invasive surgery.

The preferred techniques for hernia repair, therefore, employ laparoscopy and endoscopy, and so avoid many of the disadvantages of more invasive techniques. In both laparoscopy and endoscopy, the necessary surgical devices and implants are introduced into the body cavity by small incisions that typically are only wide enough to allow narrow tubes to penetrate through the abdominal wall into the interior of the body cavity. The surgery is performed remotely by directing the actions of the instruments from outside the body, while observing the surgical site with optical probes also inserted into the patient. Laparoscopic and endoscopic surgery speeds the recovery of the patient, who also suffers much less overall discomfort. Such remotely conducted surgical procedures, however, generate practical difficulties for the surgeon. It is generally more difficult to insert a flexible mesh material through the small incision and position the material over the site of the hernia. Difficulties are also met when the surgeon attempts to suture the mesh material into position. The suture threads are long and have a tendency to become entangled. Further, the confined nature of a laparoscopic or endoscopic surgical site that has not been fully opened to the exterior hinders the rapid and precise placement of the sutures on the mesh material, once the latter has been positioned against the abdominal wall.

This compares with the attachment of scalp patches to the exterior surface of the head of a patient, wherein the sutures placed around the circumference of the patch may be a single suture thread interlaced between the patch and the scalp, as disclosed in Dick et al. (U.S. Pat. No. 3,914,801), and Connelly & Villani (U.S. Pat. No. 3,842,439), or by suture threads preinserted into the scalp, before attachment of the patch as disclosed by Bauman (U.S. Pat. No. 3,553,737). These disclosures, however, concern patches externally applied and require sutures to be applied after positioning a patch, or by applying sutures on the recipient patient. The external application of the patch greatly eases the technical burden of the surgeon.

A variety of methods and devices have been proposed to facilitate the securing of an implantable mesh material onto a laparoscopic or endoscopic instrument, and for positioning the mesh material within the body cavity. U.S. Pat. No. 5,333,624 to Tovey describes a device and procedure that attaches a surgical implant to an apparatus for positioning the implant within the body. U.S. Pat. No. 5,916,225 to Kugel discloses a patch with a pocket, whereby the surgeon may insert a finger into the pocket and maneuver the patch over the site of the rupture. Once in position over the herniated region, however, the surgeon still faces the problem of laparoscopically suturing the implant securely over the hernia.

In laparoscopic or endoscopic surgery, a surgeon must introduce suture threads into the body cavity through a narrow incision, position the threads against and through the implanted mesh material and tie the sutures within the confines of the body cavity. Alternatively, suture threads are prepositioned on the implant, but then have to be located and gripped by the surgical tools before the threads are passed through the abdominal wall for tying. Prepositioned suture threads, however, are difficult to locate once the implant has been placed against the site of the hernia, and long loose threads are likely to become entangled, or encounter other obstructions, thereby preventing the efficient manipulation of the threads. These problems are further exacerbated by the size of the implant and the number of sutures necessary to secure the patch. Problems similar to those of laparoscopic and endoscopic application of an implantable mesh material for the repair of a hernia may also be encountered when other implanted devices must be internally secured to a patient by minimally invasive surgical procedures.

There is, therefore, a need for a simple means of placing suture threads adjacent to the abdominal body wall and at predetermined positions so that the surgeon will be able to readily locate the suture threads for retraction through the abdominal wall. What is further needed is a method and devices for locating a suture thread in the body that does not demand extensive probing and minimizes the period of surgery.

Further, there remains a need for attaching a suture thread to an implantable device, such as an implantable patch for the repair of a hernia. A surgeon using laparoscopic and endoscopic procedures can then position sutures at predetermined sites, grasp the sutures, and pull them through a tissue for tying, without the threads entangling or otherwise resisting the surgeons actions. The present invention, therefore, is intended to provide surgically implantable devices or other prosthetic devices that have novel suturing assemblies thereon to facilitate both the grasping of the suture threads and their use without tangling and impeding securing an implantable device to the patient.

These and other objects and advantages of the invention will become fully apparent from the description and claims that follow or may be learned by the practice of the invention.

SUMMARY OF THE INVENTION

Briefly described, the present invention comprises a surgically implantable device with attached sutures and a method of applying the implant to a patient. In one aspect of the present invention, the surgically implantable device comprises a body and at least one suture thread mounted to the body and a pull-tab attached to the thread. The proximal end of the suture thread is attached to the body, and a distal region is removably attached to the body.

Another aspect of the present invention relates to a surgically implantable device such as a surgically implantable patch for the repair of a hernia, and at least one suture assembly attached to the patch. The suture assembly comprises at least one suture housing and at least one suture thread that has a proximal end attached to the patch and a distal region removably disposed within the suture housing. A pull-tab is attached to the suture thread.

Yet another aspect of the present invention relates to a suture assembly that may be attached to a surgical implant for securing the device to a patient. The surgical assembly comprises a suture thread, a pull-tab attached to the suture thread, and a suture housing. The suture thread has a proximal end attached to a surgical implant and a distal region, wherein the distal end of the suture thread is detachably attached to a surgically implantable device.

Still another aspect of the present invention relates to a method of surgically attaching a surgical implant to a patient, comprising the steps of selecting a surgical implant that has at least one suture thread attached thereon, inserting the surgical device through an incision in the abdominal wall and into the body cavity of a patient, placing the device so as to place the suture assembly adjacent to the abdominal wall, acquiring the suture thread by means of a pull-tab located thereon, pulling the suture through the abdominal wall and securing at least one of the suture threads to the patient.

The present invention addresses the need of a surgeon to readily locate suture threads that are attached to a surgically implantable device before implantation into the patient. The present invention further addresses the need to grasp the suture threads and pass them through body tissues by laparoscopic or endoscopic surgery, without the predisposed suture threads entangling or otherwise resisting the surgical procedure. The present invention addresses these needs by removably confining suture threads to an implantable device while the proximal ends of the threads are securely fixed to the implanted device. The present invention further includes novel pull-tabs that allow the grasping of a suture thread and its detachment from the implantable device, while one end of each thread remains attached to the implantable device.

Additional objects, features, and advantages of the invention will become more apparent upon review of the detailed description set forth below when taken in conjunction with the accompanying drawing figures, which are briefly described as follows.

DESCRIPTION OF THE INVENTION

Figure 1A:
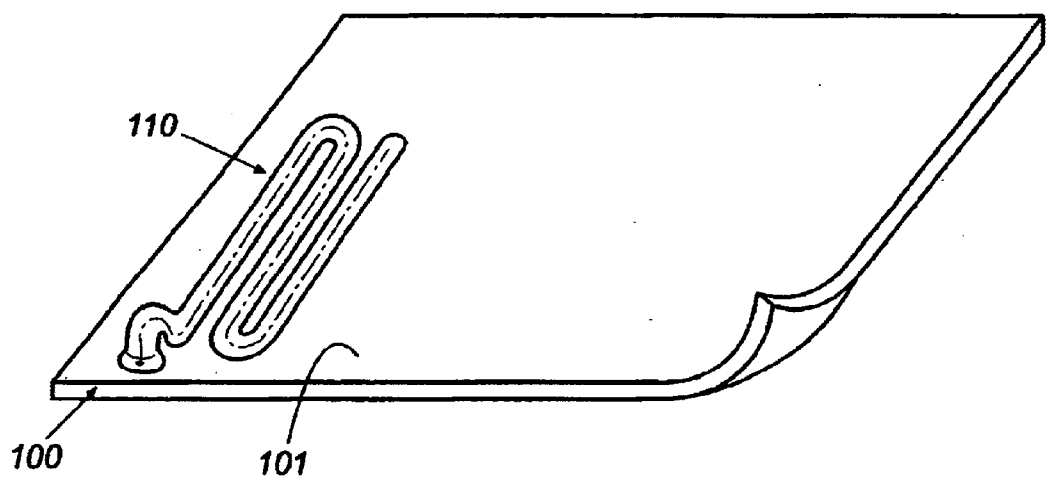
FIG. 1A. is a top perspective view illustrating an embodiment of a surgically implantable patch made in accordance with the present invention.

A full and enabling disclosure of the present invention, including the best mode known to the inventor of carrying out the invention is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

The present invention is directed to the problem of locating, by laparoscopic or endoscopic surgical procedures, suture threads that have been attached to a surgically implantable device before insertion of the device into the body cavity of a patient. With reference to FIGS. 1A–5B, the present invention provides a surgically implantable device 100 having a first surface 101 and a second surface 102 and at least one suture assembly 110 disposed on the first surface 101. Since a suture assembly 110 is attached to the surgically implantable device 100 during manufacture, the surgeon will be aware of the position of the assembly 110 relative to the surgically implantable device 100 and the patient, even though the surgically implantable device 100 is inserted into the abdominal body cavity of the patient. When a plurality of suture assemblies 110 are attached to a surgically implantable device 100, a surgeon will also be aware of the positions of the assemblies 110 relative to each other. The present invention enables the surgeon to readily locate the suture threads for securing the surgically implantable device 100 to the patient by laparoscopic or endoscopic surgical devices. The present invention further provides a pull-tab 115, whereby a suture thread 111 may be grasped for extracting the suture thread 111 from a suture housing 114 and for pulling the thread 111 through the abdominal wall or other tissue for subsequent securing of the surgically implantable device 100 to the patient. Although the illustrated embodiments of the present invention are intended for the repair of a hernia, especially a hernia of the abdominal wall, the present invention also contemplates that the disclosed suturing assembly 110 can be applied to other surgically implantable devices such as, but not limited to, prosthetic vascular blood vessels, penile implants, implants for reconstructive surgery or dental implants that can be secured by suturing.

The present invention further comprises a mesh patch, or a laminated patch comprising a first layer 103 and a second layer 104, and at least one suture assembly 110 thereon, wherein each suture assembly 110 comprises a suture thread 111 and a suture housing 114. The proximal end 112 of each suture thread 111 is attached to the patch at a pre-determined position. While it is anticipated that in a preferred embodiment of the invention a suture assembly 110 will be attached to a first surface 101 of the surgically implantable device 100 contacting the abdominal wall, the present invention also contemplates that a suture assembly 110 can be located on a second surface 102 of the surgically implantable device 100 and which is not in contact with the abdominal wall of the patient.

A pull-tab 115 is slideably attached to, or formed by, the suture thread 111. The pull-tab 115 can be a detachable region of the suture housing 114, connected to the suture housing 114 by at least one frangible join 116 and 117, and slideably disposed over or around the suture thread 111. An alternative embodiment of the pull-tab 115, contemplated by the present invention, is a loop of the suture thread 111 that may be hooked by a surgical grasping tool 130.

The distal region 113 of the thread 111 is enclosed within, but not secured by, a suture housing 114. The suture housing 114 may be on a first surface 101 or a second surface 102 of the surgically implantable device 100, embedded within a layer of the surgically implantable device 100, or sandwiched between two adjacent laminated layers of the surgically implantable device 100. When a pulling force is applied to the pull-tab 115, the suture thread 111 is withdrawn from the suture housing 114 while leaving the proximal end 112 of the suture thread 111 attached to the surgically implantable device 100. The pull-tab 115 is grasped or hooked by a surgical tool 130. The suture thread 111 then moves relative to the grasping tool 130 by sliding through the held pull-tab 115, or if the pull-tab 115 is a loop, by passing over the grasping tool 130.

For surgical implantation, a pliable surgically implantable device 100 can be rolled along any axis so that the diameter of the roll will allow insertion of the patch into a body cavity through a narrow incision typical for laparoscopic or endoscopic surgery. Alternatively, the surgically implantable device 100 could be packaged for insertion through a laparoscopic or endoscopic incision. The surgically implantable device 100 can then be unrolled or removed from a package within the body cavity and positioned across and beyond the site of a hernia, thereby placing the suture assembly 110, and a pull-tab 115 thereon, adjacent to the abdominal wall. A laparoscopic or endoscopic grasping tool 130 is inserted through the abdominal wall and a suture pull-tab 115 is grasped. The grasping tool 130 is then retracted, pulling the pull-tab 115 away from the surgically implantable device 100 and thereby dragging the distal region 113 of the suture thread 111 from the suture housing 114. The suture thread 111 held by the grasping tool 130 can then be drawn into or through the tissues of the abdominal wall and secured thereto. Generally, the grasping tool 130 will maintain a grip on the pull-tab 115, remove the pull-tab 115 from the suture thread 111 and dispose of the pull-tab 115 outside the body of the surgical patient, rather than have the pull-tab 115 be left free in the body cavity. Most commonly, in hernia repair operations, suture threads are tied subsutaneously, although the present invention contemplates that suture threads retracted through the entire body wall can be tied outside the body.

The term "surgically implantable device" as used herein, refers to, but is not limited to, pliable sheets for the covering of a hernia. The terms "surgically implantable device" or "patch" are also understood to include any prosthesis or implant that can be secured to a patient by means of sutures. The term "patch" as used herein also refers to, but is not limited to, a monolayer or a laminate of at least two layers. At least one layer of the patch may comprise a mesh having a structure of individual fibers interlaid in an identifiable manner, or a "non-woven fabric or web" wherein the individual fibers are not interlaid in an identifiable manner. A mesh or any other layer of a patch or implant may comprise filaments or films of synthetic material such as, but not limited to, polypropylene, polytetraflouroethylene (PTFE), rayon, nylon or any other biologically acceptable material, or a synthetic or natural material, or any combination thereof. The implanted material may be progressively degraded and absorbed by the patient's tissues. Such absorbable materials include, but are not limited to, collagen, a cultured skin or cell layer or any other pliable material or combination thereof that is known to one of ordinarily skill in the art, and which is acceptable for implantation in a patient. Mesh fabrics for use in connection with hernia repair are disclosed in U.S. Pat. Nos. 3,054,406; 3,124,136; 4,193,137; 4,347,847; 4,452,245; 4,520,821; 4,633,873; 4,652,264; 4,655,221; 4,838,884; 5,002,551; 6,042,592 and 6,090,116, incorporated herein by reference in their entireties.

The term "prosthesis" as used herein refers to any device that can be implanted into a patient and secured to the patient by sutures. A prosthesis can be, but is not limited to, a vascular prosthesis, a vascular stent, a membrane, a cardiac valve, a penile implant, a reconstructive surgery implant, or any other natural or artificial device or membrane for implantation into a patient to which a suture assembly of the present invention can be attached. Such a "prosthesis" can be of any material such as, but not limited to, polypropylene, polytetraflouroethylene (PTFE), rayon, nylon or any other biologically inert material, or a synthetic or natural material that, when implanted in a patent, may be progressively absorbed by the patient's body. Such absorbable materials include, but are not limited to, collagen or any other pliable material known to one of the ordinarily skill in the art, and which is acceptable for implantation in a patient.

The term "suture thread" as used herein refers to a thread or thread-like filament that is flexible and may be tied with another thread. The suture thread may comprise any synthetic or natural material such as, but not limited to, polypropylene, PTFE, or any other synthetic or natural material known to one of ordinary skill in the art that will provided a suture thread suitable for use in a patient without adverse biological activity or reactivity, and which can be withdrawn from a suture housing.

The term "suture housing" as used herein refers to any means to enclose a suture thread or a plurality of threads and which will not resist removal of the thread from the housing by friction or entangling of the thread within the housing. The housing may comprise a tube or cannula that may be linear or folded, or a sac. It is within the scope of the present invention for the "suture housing" to further comprise an unbonded region between at least two layers of a laminated implantable patch and forming a lumen or sac that encloses the thread bonding. It is also within the scope of the present invention that the "suture housing" be a region of bonding by an adhesive or other means that will allow the bonded region of the suture thread to be detached from the surgical implant. Suture housings include, but are not limited to, a cannulae or sac of silicane, polypropylene, PTFE or any other material known to one of ordinary skill in the art, or any combination thereof, that will not restrict withdrawal of a suture thread from the housing. The suture housing may further comprise a laminate wherein the layers are composed of any material such as, but not limited to, a mesh, a PTFE layer or any combination thereof that may form a biologically implantable patch.

The term "frangible area" as used herein refers to an area of weakness that allows the separation of a pull-tab and a suture housing. The area of weakness may be, but is not limited to, a wall of reduced thickness, an area of perforations, or any other means that will allow breaking of the frangible area.

The term "suture assembly" as used herein refers to a suture thread and a pull-tab wherein the distal region of the suture thread is removably attached to a surgically implantable device, either by bonding directly to the surface of the implantable device or by being enclosed in a suture housing.

The term "package" as used herein refers to any tube, sachet, envelop of other container that may contain a surgically implantable device and which will allow the implantable device to be inserted into a patient.

The terms "endoscopy" or "endoscopic" as used herein refer to the insertion of a lighted optic tube into a cavity or lumen of a patient. The lighted optic tube may further comprise surgical tools for performing surgery.

The terms "laparoscopy" or "laparoscopic" as used herein refer to the insertion of a surgical tool or device through incisions of the abdomen for conducting surgical procedures therein.

The term "hernia" as used herein refers to the protrusion of a bodily tissue or organ through any opening in a membrane or other tissue, whether the opening is natural, abnormal or normal, the result of surgery or a trauma. A frequently encountered hernia occurs in the region of the superficial inguinal ring of the groin region. When the intestine protrudes through the inguinal opening in the abdominal cavity wall, one has a direct or indirect inguinal hernia. A femoral hernia results from the intestine protruding through the abdominal wall in the region of the femoral ring. A hiatal hernia is where a portion of the stomach protrudes through the esophageal hiatus into the thoracic cavity.

Embodiments of the implantable patch of the present invention are illustrated in FIGS. 1A–5C. Referring to FIGS. 1A–5C, a surgically implantable device 100 is shown as having a first surface 101 and a second surface 102 and a single suture assembly 110 located on the first surface 101.

Referring now to FIG. 1A, an embodiment of the present invention is shown having a single suture assembly 110 for illustrative purposes only. It will be readily understood by one of ordinary skill in the art, however, that a plurality of suture assemblies 110 may be required for the secure attachment of the implantable patch in a patient. It is contemplated by the present invention, however, that a single suture thread 111 may be used by repeated passes of the thread 111 through the patient's tissue and the implantable patch 100 to secure the patch 100 around its circumference. It is not, however, the intention of the present invention to limit the number of suture assemblies 110 on a patch 100. It will be understood by one of ordinary skill in the art that the number and position of the suture assemblies 110 may vary depending on the severity, size, and location of the hernia. One of ordinary skill in the art will recognize that the suture assemblies 110 are sufficient in number and size that when the patch 100 is secured to the patient, the patient's intestine or other internal organ will be unable to protrude between the secured patch 100 and the abdominal wall of the patient.

Figure 1B:
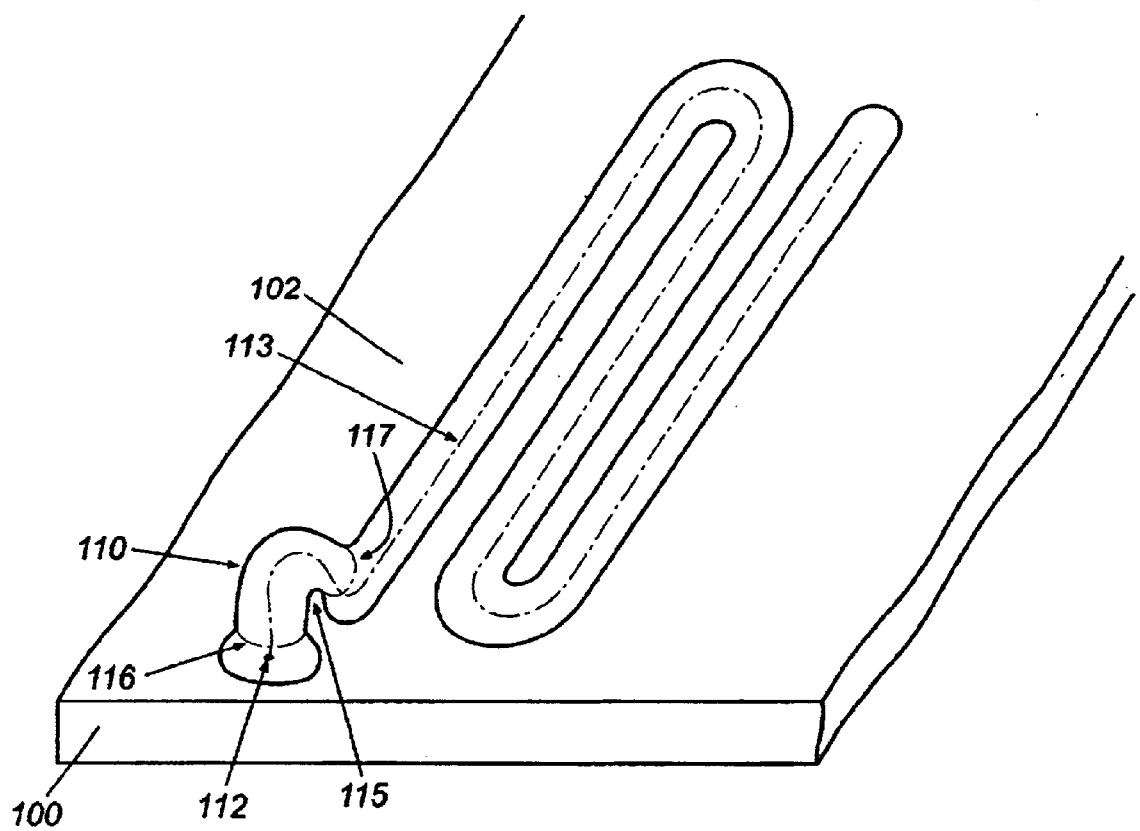
FIG. 1B illustrates one embodiment of a suture assembly made in accordance with the present invention.

Referring now to FIG. 1B, an embodiment of the suture assembly 110, as contemplated by the present invention, is illustrated. The suture assembly 110 comprises a suture thread 111 having a proximal end 112 attached to the first surface 101 of the surgically implantable device 100, and a distal region 113. The suture thread 111 may be of any length that will allow for the securing of the surgically implantable device 100 to the patient. The proximal end 112 of the suture thread 111 may be secured to the first surface 101 of the surgically implantable device 100 by an adhesive, heat bonding or embedding the suture thread 111 in the surgically implantable device 100 by any means known to one of skill in the art that will prevent the suture thread 111 from detaching from the surgically implantable device 100 when the surgically implantable device 100 is tied to the patient.

The distal region 113 of the suture thread 111 is enclosed in, but not secured by, a serpentine cannula suture housing 114 attached to the first surface 101 of the surgically implantable device 100. The length of the suture housing 114 is at least as long as that of the suture thread 111 that is enclosed within the housing 114. Suture housings 114 may also be attached to the second surface 102 of the surgically implantable device 100, depending on the site of the surgically implantable device, as selected by the surgeon. The suture housing 114 may be attached to the surgically implantable device 100 by any method known to one of skill in the art such as, but not limited to, an adhesive, heat bonding or by mechanical means such as clips. It is further contemplated by the present invention that the distal region 113 of the suture thread 111 is removably attached to the implantable device by an adhesive that resists detachment of the suture thread 111 from the implantable device or patch 100. Force applied by the surgeon, however, will detach the distal region 113 of the thread 111.

The suture housing 114 as shown in FIG. 1B, enclosing suture thread 111, is looped to form a pull-tab 115 slideably disposed totally or partially around the suture thread 111. The region of the suture housing 114 forming the pull-tab 115 is attached to the first surface 101 of the surgically implantable device 100. Frangible areas 116 and 117 are provided to allow the surgeon to detach the pull-tab 115 from the surgically implantable device 100 and the suture housing 114. The frangible areas 116 and 117 may be selected from a complete or partial ring of perforations around the suture housing 114, or regions of mechanical weakness, or any other means known to one of ordinary skill in the art that will allow the pull-tab 115 to be removed from the surgically implantable device 100. In the embodiment of the present invention as shown in FIG. 1B, the proximal end 112 of the suture thread 111 is secured to the surgically implantable device 100. The pull-tab 115, when detached by breaking of the frangible areas 116 and 117, can freely slide over the suture thread 111 as the distal region 113 of said thread 111 is pulled from the suture housing 114.

Figure 1C:
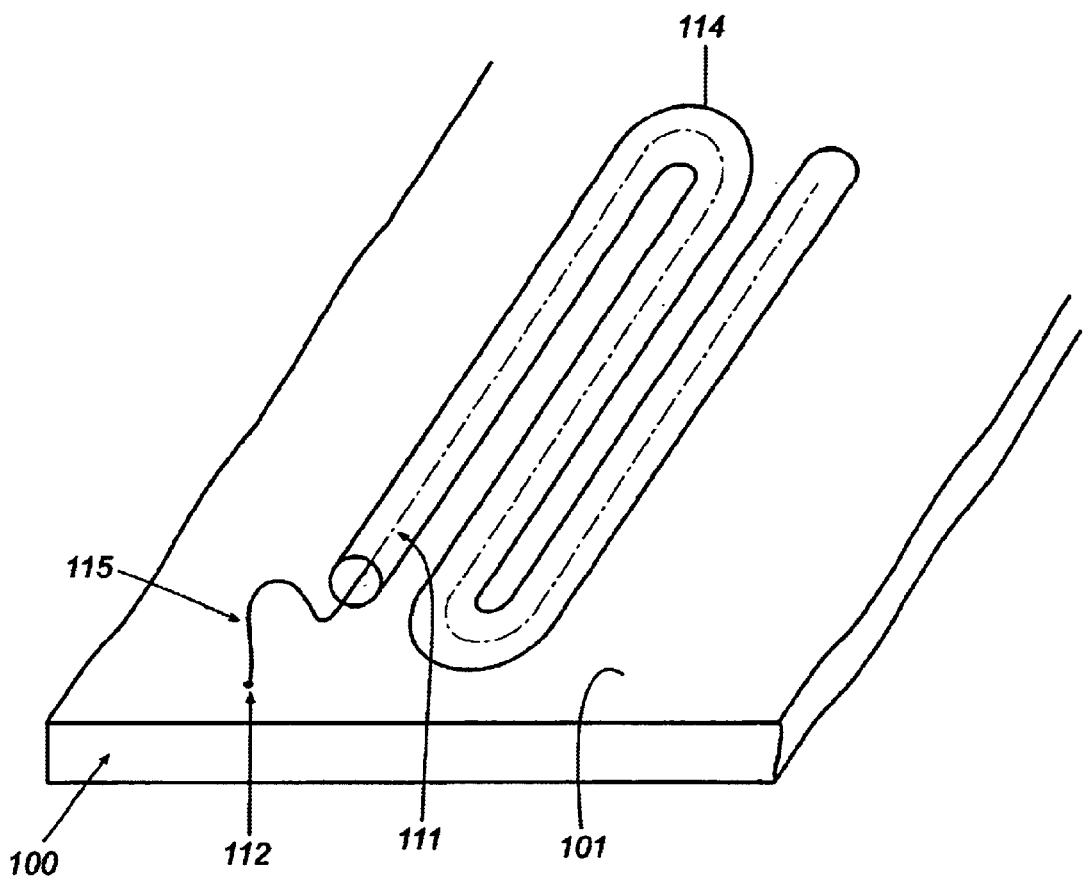
FIG. 1C illustrates another embodiment of a suture assembly made in accordance with the present invention.

In still another preferred embodiment of the present invention, as illustrated in FIG. 1C, the pull-tab 115 is a folded region of the suture thread 111 that is not enclosed by the suture housing 114. In this embodiment, the proximal end 112 of the suture thread 111 is secured to the first surface 101 of the surgically implantable device 100 by an adhesive, heat bonding, or embedding in the surgically implantable device or by any other means known to one of skill in the art and which will prevent the suture thread 111 from detaching from the surgically implantable device 100 when said surgically implantable device 100 is secured to the patient. The suture thread 111 is not secured within the suture housing but may be pulled from said housing by means of the pull-tab 115.

Figure 1D:
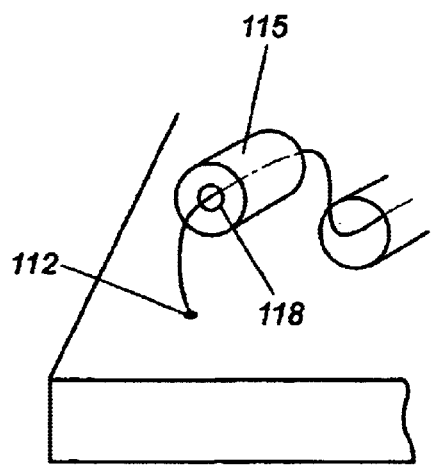
FIG. 1D illustrates another embodiment of the pull-tab made in accordance with the present invention.

Referring now to FIG. 1D, showing yet another embodiment of the present invention, the pull-tab 115 is not joined to the suture housing 114, but is slideably disposed on the suture thread 111, between the proximal end 112 of the thread 111 that is attached to the surgically implantable device 100, and the suture housing 114.

Figure 2A:
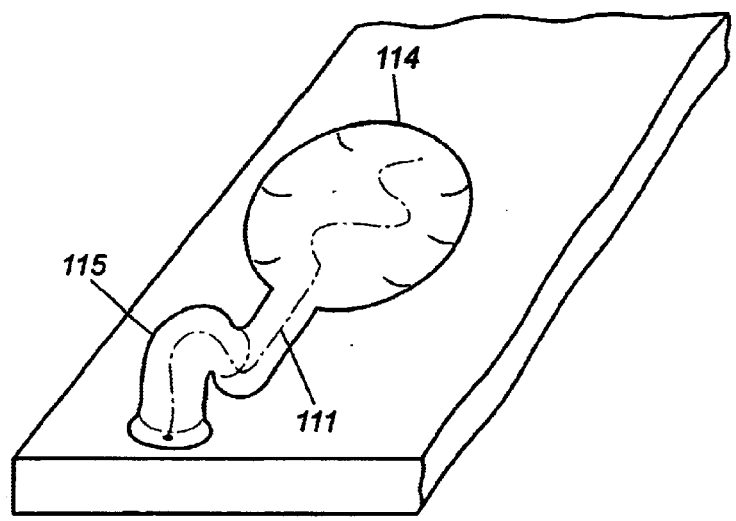
FIG. 2A illustrates an embodiment of the suture assembly wherein the housing is a sac made in accordance with the present invention.
Figure 2B:
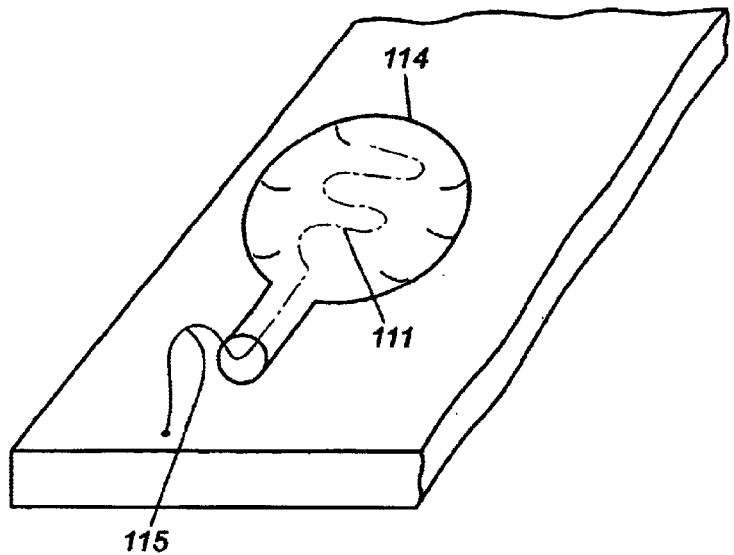
FIG. 2B illustrates yet another embodiment of the suture assembly wherein the housing is a sac made in accordance with the present invention.

Other preferred embodiments of the present invention are illustrated in FIGS. 2A, 2B, 2C and 2D. It is not, however, the intention of the present invention to limit the suture assembly to the embodiments as shown in FIGS. 1A–2D. The present invention, therefore, contemplates any form or dimensions of the suture housing 114 and pull-tab that allow the thread 111 to be withdrawn without restriction. Referring to FIG. 2A, the suture housing 114 is a sac enclosing a suture thread 111 therein. In this embodiment the pull-tab 115 is a folded region of the housing 114. In FIG. 2B the suture housing 114 is a sac, and the pull-tab 115 is a fold in the suture thread 111.

Figure 2C:
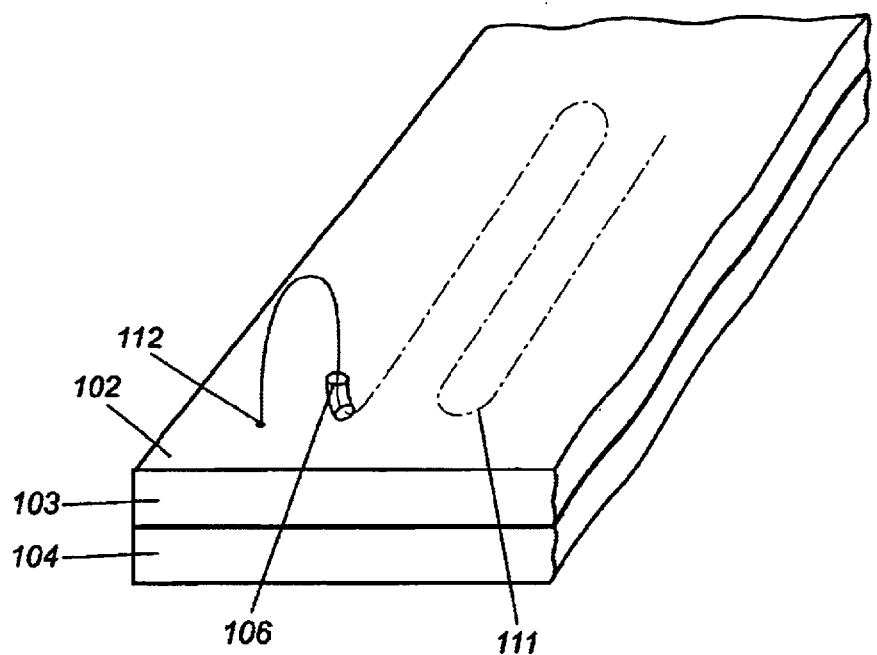
FIG. 2C illustrates an embodiment of the suture assembly made in accordance with the present invention.

In the preferred embodiment shown in FIG. 2C, the suture thread 111 is enclosed between, but not fixed within, a first layer 103 and a second layer 104 laminated to form the surgically implantable device 100. The suture thread slideably passes through the first layer by any means such as, but not limited to, a hole 106. A fold in the thread 111 forms a pull-tab 115. The proximal end 112 of the thread 111 is attached to the surgically implantable device 100 by any means known to one of ordinary skill in the art.

Figure 2D:
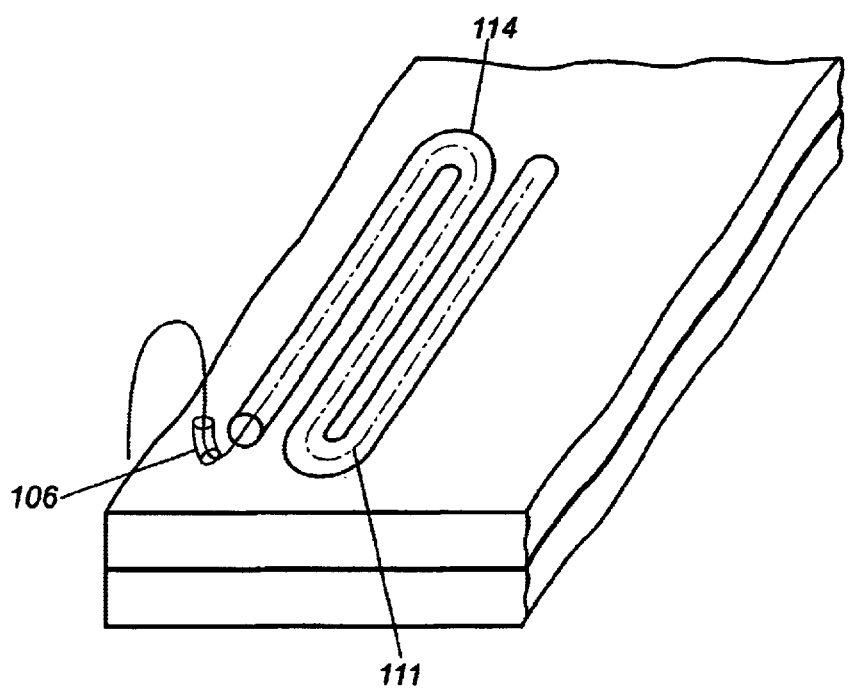
FIG. 2D illustrates yet another embodiment of the suture assembly made in accordance with the present invention.

In yet another preferred embodiment of the present invention, as shown in FIG. 2D, the suture thread 111 is attached at its proximal end 112 to the surgically implantable device 100, and is enclosed within, but not secured by, a suture housing 114 formed by an unbonded region between a first layer 103 and a second layer 104 that comprise two layers of the laminated surgically implantable device 100. The suture thread slideably passes through the first layer by any means such as, but not limited to, a hole 106. A fold in the thread 111 forms a pull-tab 115.

The present invention is not intended to be limited as to the size and shape of the surgically implantable device 100. The dimensions and shape of the surgically implantable device 100 will be selected by the surgeon according to the requirements of the surgical procedure that implants the surgically implantable device 100 in a patient. The size and shape of the surgically implantable device 100 will depend in part on the shape and size of the hernia of the tissues of the patient and typically, but not essentially, the selected surgically implantable device 100 will cross and extend beyond the area of injury of the hernia.

The surgically implantable device selected by the surgeon to be sutured over a hernia may have any number of suture assemblies 110. The number of suture assemblies 110, however, will be selected so that when the surgically implantable device 100 has been sutured against the abdominal wall of the patient, it will prevent internal organs such as the intestine from protruding between the surgically implantable device 100 and the abdominal wall. The number of suture assemblies 110 on a surgically implantable device 100, therefore, will depend on the size and shape of the surgically implantable device 100 selected by the surgeon.

Figure 3A:
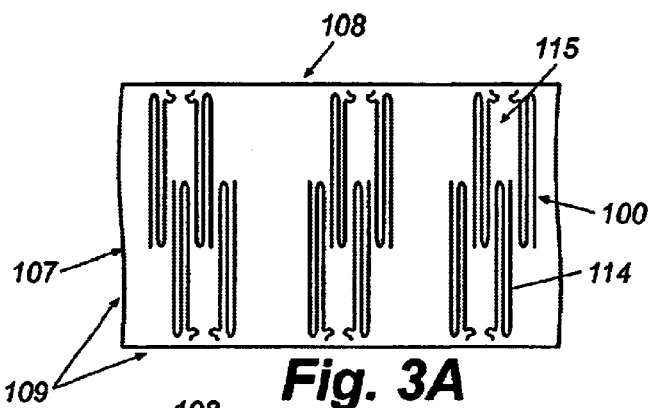
FIG. 3A. is a top perspective illustrating an embodiment of a surgically implantable device made in accordance with the present invention.
Figure 3B:
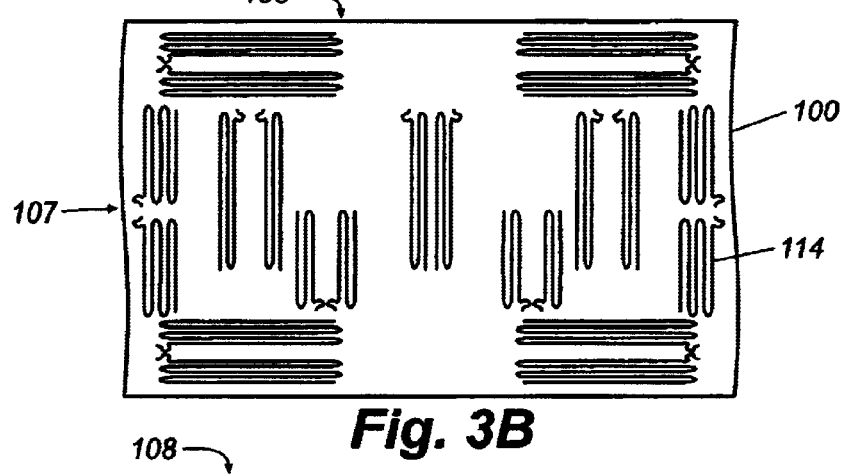
FIG. 3B. is a top perspective illustrating another embodiment of a surgically implantable device made in accordance with the present invention.
Figure 3C:
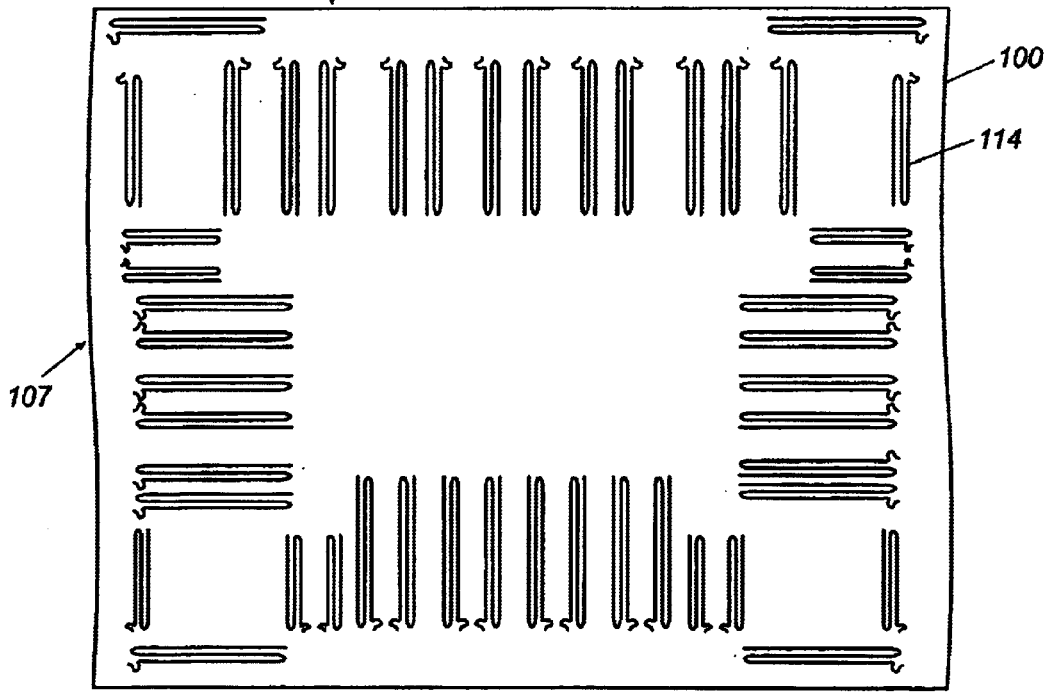
FIG. 3C. is a top perspective illustrating yet another embodiment of a surgically implantable device made in accordance with the present invention.

With reference to FIGS. 3A, 3B and 3C for illustrative purposes only, and not intended to limit the invention in any way, preferred embodiments of the implantable surgically implantable devices of the present invention are shown. In a preferred embodiment, shown in FIG. 3A, the surgically implantable device 100 has a short axis 107 and a long axis 108, and a periphery 109. In this preferred embodiment, the suture assemblies 110 are disposed on the surgically implantable device 100 in five pairs. The positions of the pull-tabs 115 determine the positions for placing the tied sutures in the abdominal wall. The elongated serpentine suture housings 114 of a pair of suture housings 114 are parallel to each other. Although the serpentine folding of the suture housing 114 allows the housings 114 to be placed close to each other, it is within the scope of the present invention for other folded or unfolded configurations of the suture housing 114 that will allow a required number of housings 114 to be disposed on a surgically implantable device 100. The lengths of the suture threads 111 and the enclosing suture housings 114 and their positions on the surgically implantable device 100 can be selected by the surgeon before implantation of the surgically implantable device 100 into the patient and will depend upon the size and shape of the hernia to be covered by the surgically implantable device 100.

In another preferred embodiment, shown in FIG. 3B, the surgically implantable device 100 has a short axis 107 and a long axis 108. In this preferred embodiment, the suture assemblies 110 are disposed on said surgically implantable device 100 in ten pairs.

In yet another preferred embodiment of the present invention, shown in FIG. 3C, the surgically implantable device 100 has a short axis 107 and a long axis 108. In this preferred embodiment, the suture assemblies 110 are disposed on said surgically implantable device 100 in 24 pairs.

In the preferred embodiments illustrated in FIGS. 3A–3C, and in all other embodiments contemplated by the present invention, the positions of the pull-tabs 115 determine the positions for placing the tied sutures in the abdominal wall.

The number and positions of the required suture assemblies 110 depend on the size and shape of the surgically implantable device 100 selected by the surgeon. One of ordinary skill in the art will recognize that a preferred disposition of the pull-tabs 115 is adjacent to the periphery 109 of the surgically implantable device 100. With reference to FIGS. 3A–3C, it will be further recognized that pull-tab 115 can be placed at any position on the surgically implantable device 100, and on the first surface 101 or the second surface 102, and so disposed that when suture threads 111 are tied in the abdominal wall, the surgically implantable device 100 will prevent the intestine or other internal anatomical structures from protruding through the abdominal wall.

The present invention further contemplates that the suture housing 114 may be any shape or size that will accept a suture thread 111. Although the suture housings 114 of the embodiments of the present invention, as illustrated in FIGS. 1A–3C are elongated cannulae, the suture housing 114 may be round, rectangular or any other shape or size that will enclose at least one suture thread 111 and allow the suture thread 111 to be withdrawn smoothly and without entangling.

It is further contemplated by the present invention that the distal region 113 of the suture thread 111 may be removably attached to the first surface 101 of the surgically implantable device 100 without being enclosed in a suture housing 114. It is contemplated that the suture thread 111 may be removably attached to the surgically implantable device 100 by an adhesive, heat bonding or any other method known to one of ordinary skill in the art that allows the distal region 113 suture thread 111 to be removed from the first surface 101.

It is also contemplated that the present invention provides a suture assembly 110 that can also be attached to surgically implanted prostheses other than for treatment of a hernia of the abdominal wall. By way of illustration only, the suture assembly 110 of the present invention may be applied to a vascular prosthesis to allow a surgeon to implant and secure a prosthetic blood vessel having pre-selected positions for the sutures threads 111 thereon. The suture assembly 110 of the present invention may be applied to other implantable devices.

The present invention also provides a method of applying the implantable surgically implantable device 100 and suture assembly 110 attached thereon to or cover a split of an internal tissue of a patient, such as, but not only, a hernia of the abdominal wall. The pliable surgically implantable device 100 to be applied to cover an opening in the internal abdominal wall of a patient can be rolled, folded or otherwise configured so that the surgically implantable device 100 can be inserted into the body cavity of a patient through an laparoscopic or endoscopic incision through the body wall. The present invention further contemplates that the surgically implantable device 100 may be enclosed in a package device for the insertion into the patient, whereupon the surgically implantable device 100 is withdrawn from the package.

Figure 4A:
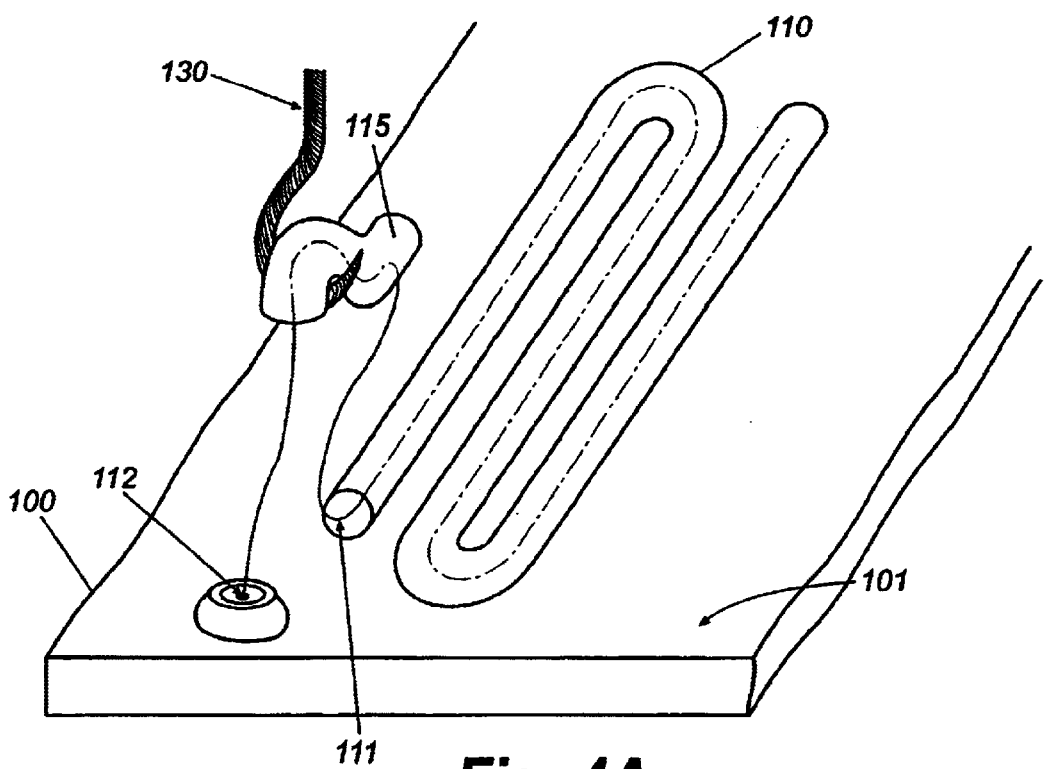
FIG. 4A. illustrates a method of locating a suturing thread with a grasping tool in accordance with the present invention.

The present invention further provides a method of withdrawing a suture thread 111 from a suture housing 114 disposed on or within an implantable patch 100. In a preferred embodiment, with reference to FIG. 4A, the suture housing 114 comprises a serpentine cannula enclosing a suture thread 111. The suture housing 114 further comprises a pull-tab 115 and frangible areas 116 and 117, as illustrated also in FIG. 1B. With reference to FIG. 4A, once the patch 100 has been unrolled or otherwise placed at a selected position in the body of a patient, a grasping tool 130 is used to grasp the pull-tab 115. The present invention should not be construed as limiting the method to using a grasping tool 130 having a hook. Any tool known to one of ordinary skill in the art such as, but not limited to, a hook, a forceps device or any other means capable of grasping or holding the pull-tab 115 and thereby allowing the pull-tab 115 to be separated from the suture housing 114, can be used.

As shown in FIG. 4A, the pull-tab 115 is detached from the suture housing 114 and the pull-tab 115 pulled away from the patch 100 after the frangible areas 116 and 117 are broken. The pull-tab 115 slideably moves relative to the suture thread 111, which is thereby pulled from the suture housing 114 while the proximal end 112 of the thread 111 remains attached to the patch 100.

Figure 4B:
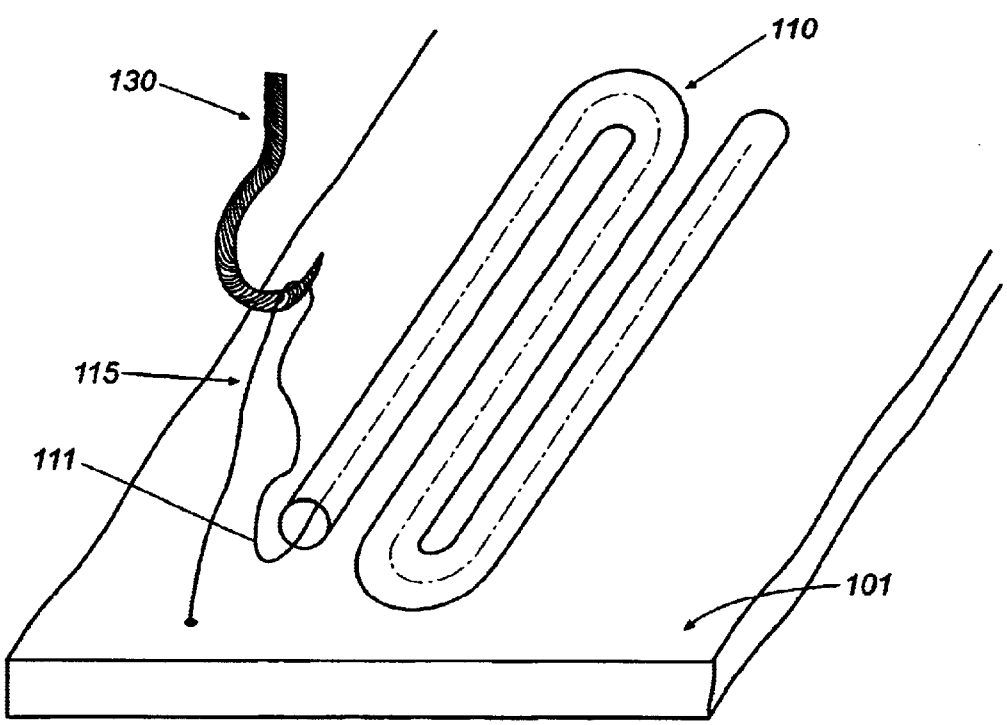
FIG. 4B. illustrates another method of locating a suturing thread with a grasping tool in accordance with the present invention.

In another preferred embodiment of the present invention shown in FIG. 4B, the grasping tool 130 is a hook that hooks a pull-tab 115 formed by a loop of the suture thread 111, whereupon the suture thread 111 slideably passes over the hook and the thread 111 is pulled from the suture housing 114 into the abdominal wall of the patient.

Figure 5A:
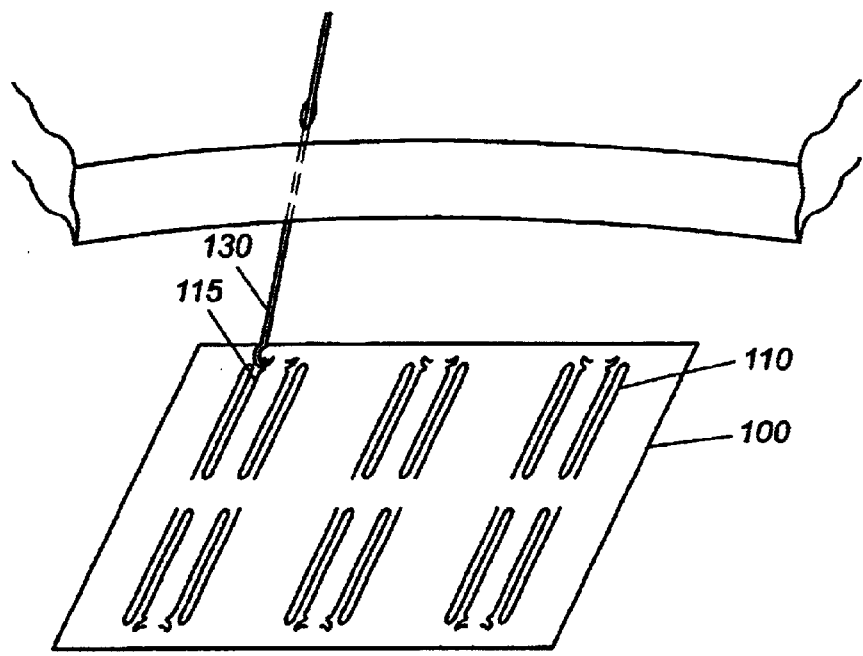
FIG. 5A illustrates the locating of a pull-tab attached to a suture thread in accordance with the present invention
Figure 5B:
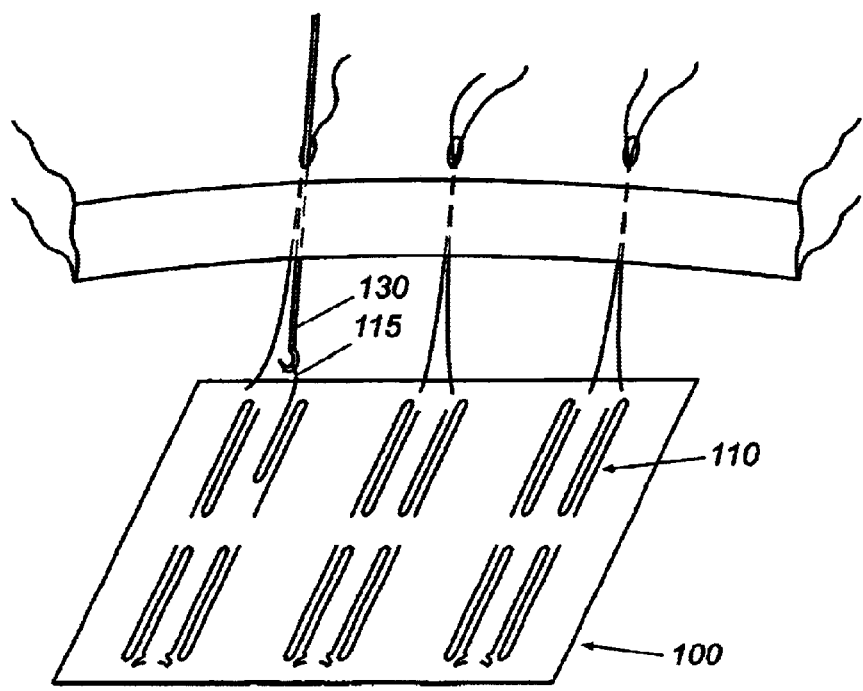
FIG. 5B illustrates the extraction of a suture thread from a suture housing by means of a pull-tab and a grasping tool in accordance with the present invention.

A method of applying a patch with a plurality of suture housings 111 disposed thereon is illustrated in FIGS. 5A and 5B. The patch 100 is placed so that the plurality of pull-tabs 115 of a suture assembly 110, disposed on a surface of the patch 100, are adjacent the abdominal wall. A grasping device 130 is inserted through the abdominal wall of the patient and grasps a suture pull-tab 115. The frangible areas 116 and 117 of the suture housing 114 are broken and the pull-tab 115 is withdrawn through the body wall, thereby dragging the suture thread 111 from the suture housing 114 while the suture tread 111 slideably passes through the pull-tab 115.

The withdrawal of the remaining suture threads 111 of a patch 100 into or through the body wall is repeated around the surgically implantable device 100. It is preferred that the grasping tool 130 or any other laparoscopic or endoscopic surgical device remove the pull-tab 115 from the patient once the suture thread 111 has been pulled into position in the patient's tissue. Pairs of suture threads 111 are pulled to place the patch 100 against the interior surface of the abdominal wall. Pairs of suture threads 111 may be tied to secure the patch 100 in position.

It is contemplated by the present invention that the suture thread 111 may be drawn through the abdominal wall to the exterior of the body of the patient, whereupon the threads 111 can be tied or otherwise connected, securing the patch 100 to the inner surface of the abdominal wall. Alternatively, the threads 111 may be withdrawn only to the subcutaneous tissue layer and secured together therein.

With respect to the above description, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawing and described in the specification are intended to be encompassed by the present invention. Further, the various components of the embodiments of the invention may be interchanged to produce further embodiments and these further embodiments are intended to be encompassed by the present invention.

Although the invention has been described in detail for the purpose of illustration, it is understood that such detail is solely for that purpose, and variations can be made therein by those skilled in the art without departing from the spirit and scope of the invention which is defined by the following claims.

I claim:

1. A surgically implantable device, comprising:
    a body;
    at least one suture thread extendably mounted to the body, wherein the suture thread has a proximal end attached to the body, and a distal region removably attached to the body;
    a suture housing disposed on the body, wherein the distal region of the suture thread is removably contained within said suture housing; and
    a pull-tab connected to the at least one suture thread for completely removing the suture thread from the suture housing.
2. The device of claim 1, wherein the body is a surgical implant, patch, cover or dressing.
3. The device of claim 1, wherein the body is a surgically implantable patch for the repair of a hernia.
4. The device of claim 3, wherein the surgically implantable patch is a monolayer selected from a mesh, a porous film, a nonporous film or a combination thereof.
5. The device of claim 3, wherein the surgically implanted patch is a mesh of interwoven or interlaid filaments, and wherein the mesh comprises a natural or a synthetic material or a combination thereof.
6. The device of claim 3, wherein the surgically implantable patch is a laminate comprising a first layer and a second layer.
7. The device of claim 6, wherein at least one layer of the laminate is a mesh comprising a synthetic material selected from polypropylene or polytetraflouroethylene (PTFE) or a combination thereof, and the second layer of the laminate comprises PTFE.
8. The device of claim 1, wherein the body is a surgically implantable device selected from a prosthesis, a vascular prosthesis, a cardiovascular implant, a vascular stent, a bone repair implant, and an implantable medical device, organ, tube, and membrane.
9. The device of claim 1, further comprising a frangible area disposed between the pull-tab and the housing.
10. The device of claim 1, wherein the pull-tab is slideably disposed on the suture thread.
11. The device of claim 1, wherein the pull-tab is attached to the suture thread.
12. The device of claim 1, wherein the pull-tab is a looped region of the suture thread.
13. The device of claim 1, wherein the device is contained in a package device.
14. The device of claim 1, wherein the suture housing comprises a cannula.
15. The device of claim 1, wherein the suture housing is a sac.
16. The device of claim 1, wherein the suture housing is a compartment defined by the surgically implantable patch.
17. A surgically implantable device, comprising:
    a body;
    at least one suture thread extendably mounted to the body, wherein the suture thread has a proximal end attached to the body, and a distal region removably attached to the body;
    a suture housing disposed on the body, wherein the distal region of the suture thread is removably contained within said suture housing and wherein the distal region of the suture thread is removably attached to the body by heat bonding or an adhesive; and
    a pull-tab connected to the at least one suture thread for pulling the suture thread from the suture housing.
18. A surgically implantable device, comprising:
    a surgically implantable patch;
    at least one suture assembly attached to the patch, wherein the suture assembly comprises at least one suture housing;
    at least one suture thread having a proximal end attached to the patch and a distal region removably disposed within the suture housing; and
    a pull-tab attached to the suture thread for completely removing the suture thread from the suture housing.
19. A suture assembly for attaching a surgical implant to a patient, comprising:
    a suture thread;
    a suture housing attached to the surgical implant and removably containing the suture thread; and
    a pull-tab attached to the suture thread, wherein the pull-tab is adapted to be engaged and pulled for completely removing the suture thread from the suture housing.
20. The suture assembly according to claim 19, further comprising a frangible area disposed between the pull-tab and the housing.
21. The suture assembly according to claim 19, wherein the pull-tab is not attached to the suture housing and is slideably disposed on the suture thread.
22. The suture assembly according to claim 19, wherein the pull-tab for completely removing the suture thread from the suture housing comprises a fold of the suture thread.
23. The suture assembly according to claim 19, wherein the suture housing is attached to a surgical implant.
24. The suture assembly according to claim 19, wherein the suture housing is a cannula.
25. The suture assembly according to claim 19, wherein the suture housing is a sac.
26. The suture assembly according to claim 19, wherein the suture housing is defined by a bonded area between two layers of a surgical implant.
27. A method of surgically securing a surgically implantable device to a patient, comprising the steps of:
    a) selecting a surgically implantable device according to claim 1;
    b) inserting the surgically implantable device through an incision in the patient;
    c) placing the surgically implantable device so as to place the at least one suture thread adjacent to a selected tissue of the patient;
    d) acquiring the at least one suture thread by means of a pull-tab attached thereon and completely removing the suture thread from the suture housing;

e) moving the at least one suture thread through the tissue; and f) securing the at least one suture thread so as to attach the surgically implantable device to the patient.

28. The method according to claim 27, further comprising the step of repeating steps d) and e).

29. The method according to claim 27, wherein the surgically implantable device is an implantable patch.

30. The method according to claim 27, wherein the surgically implantable device is configured so as to pass through a laparoscopic incision.

31. A method of surgically securing a surgically implantable device to a patient, comprising the steps of:

a) selecting a surgically implantable device comprising a body, at least one suture thread extendably mounted to the body, wherein the suture thread has a proximal end attached to the body, and a distal region removably attached to the body, a suture housing disposed on the body, wherein the distal region of the suture thread is removably contained within said suture housing, and a pull-tab operably connected to the at least one suture thread;

b) attaching the surgically implantable device to a surgical tool for insertion into a patient;

c) inserting the surgically implantable device through an incision in the patient;

d) placing the surgically implantable device so as to place the at least one suture thread adjacent to a selected tissue of the patient;

e) acquiring the at least one suture thread by means of a pull-tab attached thereon;

f) moving the at least one suture thread through the tissue; and g) securing the at least one suture thread so as to attach the surgically implantable device to the patient.

32. A method of inserting a surgically implantable device into a patient, the device including a body, a retractable thread with a proximal end attached to the body and a distal end disposed inside a housing that is affixed to the body, and a pull tab attached to the thread capable of completely removing the thread from the housing, the method comprising:

inserting the surgically implantable device into the patient;

pulling the pull tab with an insertion tool;

completely removing the distal end of the thread from the housing by the pull tab; and attaching the surgically implantable device to the patient with the thread.

* * * * *